United States Patent [19]

Sherlock

[11] Patent Number: 4,551,463
[45] Date of Patent: Nov. 5, 1985

[54] COMPOSITION CONTAINING 1-PHENYL-1,8-NAPHTHRIDIN-2(1H)-ONES AND A NON-STEROIDAL ANTI-INFLAMMATORY DRUG

[75] Inventor: Margaret H. Sherlock, Bloomfield, N.J.

[73] Assignee: Schering Corporation, Madison, N.J.

[21] Appl. No.: 533,673

[22] Filed: Sep. 19, 1983

Related U.S. Application Data

[63] Continuation-in-part of Ser. No. 438,681, Nov. 3, 1982, abandoned.

[51] Int. Cl.[4] .......................................... A61K 31/435
[52] U.S. Cl. .................................. 514/300; 514/161; 514/225
[58] Field of Search ................. 424/232, 256; 546/122

[56] References Cited

U.S. PATENT DOCUMENTS

| 4,133,885 | 1/1979 | Bolhofer et al. | 546/122 |
| 4,247,554 | 1/1981 | Yamamoto et al. | 424/251 |
| 4,292,319 | 9/1981 | Tauber et al. | 424/274 |
| 4,474,766 | 10/1984 | Goldenberg et al. | 424/177 |

FOREIGN PATENT DOCUMENTS 116495  9/1977  Japan.

Primary Examiner—Jane T. Fan
Attorney, Agent, or Firm—Stephen I. Miller; Gerald S. Rosen

[57] ABSTRACT

Certain substitute 1,8-naphthyridines and 1,5,8-azanaphthyridines are useful in treating and preventing ulcers in mammals.

Methods for preparing the compounds and methods for their use are also described.

10 Claims, No Drawings

COMPOSITION CONTAINING 1-PHENYL-1,8-NAPHTHRIDIN-2(1H)-ONES AND A NON-STEROIDAL ANTI-INFLAMMATORY DRUG

This application is a continuation-in-part of copending application Ser. No. 438,681 filed Nov. 3, 1982 now abandoned.

BACKGROUND OF THE INVENTION

Japanese patent public disclosure (Kokai) No. 116495/77, Sept. 29, 1977 discloses various naphthyridine derivatives which allegedly possess analgesic, anti-inflammatory, central nervous system depressant and diuretic effects. There is no indication that the compounds disclosed in the Japanese publication have cytoprotective activity and are useful for treating and preventing ulcers.

SUMMARY OF THE INVENTION

In its first method aspect, the present invention is drawn to a method of treating ulcers in a mammal which comprises administering to a mammal in need of such treatment a therapeutically effective quantity of a compound having the structural formula I

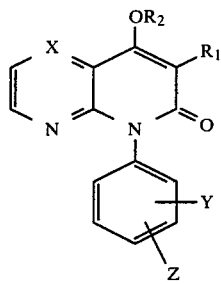

wherein
X is CH or N;
Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl-S(O)$_m$— having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;
Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;
$R_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, 2-, 3-, or 4-pyridyl, 2-, 4-, 5-pyrimidyl, 2- or 3-thienyl, 2- or 3-furanyl, carboxylic acyl having from 2 to 6 carbon atoms or alkyl having from 1 to 10 carbon atoms which may be substituted with hydroxy, halogen, —COOH, alkoxy having from 1 to 6 carbon atoms, phenyl, 2-, 3- or 4-pyridyl, 2-, 4- or 5-pyrimidyl, 2- or 3-thienyl, 2- or 3-furanyl, carboxylic acyl having from 2 to 6 carbon atoms, cycloalkyl having from 3 to 7 carbon atoms or carboxylic acyloxy having from 1 to 6 carbon atoms;

$R_2$ is hydrogen, alkenyl having from 3 to 8 carbon atoms, alkynyl having from 3 to 8 carbon atoms, carboxylic acyl having from 1 to 6 carbon atoms, $R_aR_bN(CH_2)_n$— (wherein $R_a$ and $R_b$ are hydrogen, alkyl having from 1 to 6 carbon atoms or may be joined to complete a piperidine, morpholine, piperazine or pyrrolidine ring and n is an integer of from 2 to 6) hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine.

In its second method aspect, the present invention is drawn to a method of inhibiting the formation of ulcers in mammals which comprises administering to a mammal in need of such treatment a therapeutically effective amount of a compound having the structural formula I.

The preferred value for X is CH.

The preferred values for Y are hydrogen, methoxy, trifluoromethyl and methylthio; the more preferred value is hydrogen.

The preferred values for Z are hydrogen and methyl.

The preferred values for $R_1$ are n-alkyl having from 3 to 5 carbon atoms, alkenyl having from 3 to 4 carbon atoms, omega-hydroxyalkyl having 2 to 4 carbon atoms, and omega-carboxylicacyloxyalkyl having from 6 to 9 carbon atoms; the most preferred values are n-butyl, propen-2-yl, 2-hydroxyethyl, 3-hydroxypropyl and 4-propanoyloxybutyl.

The preferred values for $R_2$ are hydrogen, carboxylic acyl of from 2 to 4 carbon atoms, hydroxyalkyl of from 2 to 4 carbon atoms, $R_aR_bN(CH_2)_n$— (wherein $R_a$ and $R_b$ are hydrogen or alkyl having from 1 to 6 carbon atoms and n is an integer from 2 to 6 carbon atoms) and the cations derived from sodium, potassium, calcium, ethanolamine, N-methylglucamine, diethanolamine, ethylenediamine, tris-(hydroxymethyl)aminomethane and lysine; the most preferred values are hydrogen, ethanoyl, propanoyl, 2-hydroxyethyl, and the cations derived from sodium, N-methylglucamine and lysine.

Preferred compounds for use in this invention are

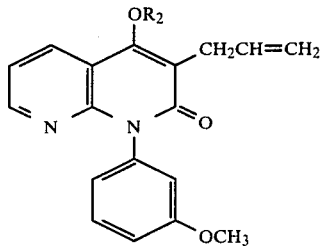

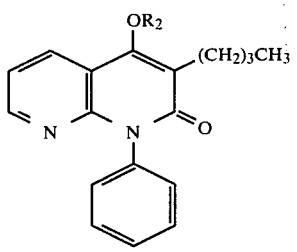

-continued

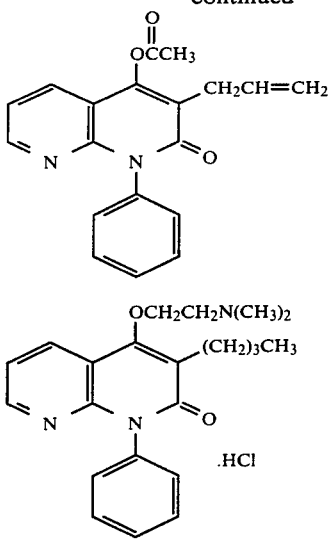

wherein R$_2$ is hydrogen or sodium Other preferred compounds are:
1-phenyl-4-propionyloxy-3(4-propionyloxybutyl)-1,8-naphthyridin-2(1H)-one;
3-(n-butyl)-4-hydroxy-1-(3-methylthiophenyl-1,8-naphthyridine-2(1H)-one;
3-(n-butyl)-4(2-hydroxyethoxy)-1-phenyl1,8-naphthyridin-2(1H)-one;
4-hydroxy-3(3-hydroxypropyl)-1-phenyl-1,8-naphthyridin-2(1H)-one.

Certain of the compounds which are utilized in the method of this invention are disclosed in Japanese patent public disclosure (Kokai) No. 116495/77, Sept. 29, 1977. The majority of the compounds utilized in the method herein are novel in view of this publication.

DESCRIPTION OF THE INVENTION

The compounds which are utilized in the method(s) of the invention may be prepared by methods known to those skilled in the art. For example, a compound having structural formula II

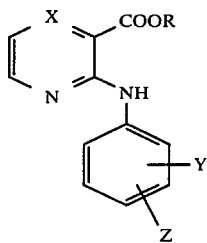   II wherein X, Y and Z are defined hereinabove and R is any convenient alkyl group may be reacted with a compound having structural formula III

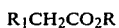   III

R$_1$CH$_2$CO$_2$R to directly produce the desired compounds wherein R$_2$ is hydrogen. This reaction is preferably accomplished by contacting the two reactants in the presence of a base such as a metal alkoxide e.g. potassium tertiary butoxide or the like, at an elevated temperature e.g. 60° to about 160° C. for a sufficient time until the reaction is substantially completed. The reaction is preferably conducted in an inert atmosphere such as nitrogen. Alternatively, the reaction may be conducted in the presence of a non-reactive solvent such as toluene, xylene etc. The so produced compounds having structural formula I wherein R$_2$ is hydrogen may be converted to compounds having other disclosed values of R$_2$ by standard procedures such as acylation, alkylation and the like.

Certain substituents present in the R$_1$ group may be interconverted by standard procedures, if desired, subsequent to the above described ring closure reaction. For example, a hydroxyl substituent may be converted to a halogen substituent such as a chlorine substituent by treatment with a halogenating agent such as thionyl chloride. Other such interconversions are contemplated herein and will be familiar to those skilled in the art.

The starting materials having structural formulas II and III are known in the art. For example, 2-phenylamino-3-pyridine carboxylic acids (II, X=CH) may be prepared as described in U.S. Pat. No. Re. 26,655. The solvent teachings of this patent are incorporated herein by reference. The requisite 2-phenylamino-3-pyrazine carboxylate esters (II, X=N) may be prepared substantially as described herein starting with a 2-amino-3-pyrazine carboxylate ester. 2-phenylamino-3-pyrazine carboxylic acid is a known compound, C.A., 75, 20154e (1971). The esters, III, may be prepared by standard procedures.

When utilized herein and in the appended claims the below listed terms, unless specified otherwise, are defined as follows:
halogen—fluorine, chlorine, bromine and iodine;
alkyl—straight and branched carbon chains containing from 1 to 10 carbon atoms;
R$_2$ is alkenyl and alkynyl having from 3 to 8 carbon atoms—alkenyl and alkynyl groups wherein the unsaturation is not at the position alpha to the oxygen to which the R$_2$ group is attached.
hydroxyalkyl and dihydroxyalkyl having from 2 to 6 carbon atoms—hydroxyalkyl and dihydroxyalkyl groups wherein the hydroxy group(s) is not substituted at the position alpha to the oxygen to which the R$_2$ group is attached.
pharmaceutically acceptable metal and amine—metals and amines that are generally recognized as being non toxic, such as sodium, potassium, calcium, aluminum, N-methylglucamine, lysine and the like;
peptic ulcers—gastric, duodenal and intestinal ulcers and irritations caused by stress, non-steroidal anti-inflammatory agents and other causes;
non-steroidal anti-inflammatory agents which cause gastrointestinal irritation and damage—aspirin, diflunisal, sulindac, piroxicam, flunixin, indomethacin, isoxicam, naproxen, sulfasalazine, ketoprofen, clonixin, phenylbutazone, ibuprofen, tolmetin sodium, fenoprofen calcium, meclofenamate sodium, niflumic and flufenamic acid and other art recognized non-steroidal anti-inflammatory agents which are known to cause gastrointestinal irritation and damage.

The active compounds utilized in the methods of this invention, are substituted 1,8-naphthyridines and substituted 1,5,8-azanaphthyridines and may exist as solvates, for example as hydrates.

The compounds of formula I are useful in treatment of peptic ulcers. The compounds of formula I have characteristics which enable them to relieve the symptoms of ulcer disease, including stress ulceration, and promote healing of the ulcers.

This anti-ulcer activity of the compounds of formula I makes them particularly useful as conjunctive therapeutic agents for coadministration with non-steriodal anti-inflammatory agents which cause gastrointestinal irritation and damage.

Non-steriodal anti-inflammatory agents are known to cause severe gastrointestinal damage which in some instances can be fatal (see Physician's Desk Reference, 37 Ed., 1306–1308 and 2002–2004). In spite of these serious side effects, use of a non-steroidal antiinflammatory agent is often the only effective treatment for severe inflammation. As a result, when treatment with a non-steroidal anti-inflammatory agent is necessary, the patient's condition and diet must be closely monitored to minimize the likelihood of severe gastro-intestinal damage.

It has now been found that when a compound of formula I is coadministered with a non-steroidal anti-inflammatory agent, the combined composition inhibits the formation of the non-steroidal anti-inflammatory induced gastrointestinal ulceration while not interfering with the anti-inflammatory activity of the non-steroidal anti-inflammatory agents. Moreover, it has been found that when this combination is administered at high doses in treating acute inflammation the anti-inflammatory activity of the compounds of formula I supplements the activity of the coadministered anti-inflammatory drug. This results in a greater anti-inflammatory therapeutic effect for the combination while at the same time providing the patient with protection against induced gastrointestinal ulceration.

Mammals in need of such prophylatic treatment for ulcers are those who are particularly susceptible to ulceration due to stress, administration of a non-steroidal anti-inflammatory agent and other causes likely to produce peptic ulceration.

In a composition aspect of the present invention, a quantity of a compound, having the structure formula I, sufficient to inhibit the formation of ulcers is combined with a therapeutically effective amount of a non-steroidal antiinflammatory drug. This composition is used to treat the inflammation while inhibiting the formation of the drug-induced ulceration recognized in the art. The composition for inhibiting the formation of nonsteroidal anti-inflammatory drug-induced ulceration comprises (a) a non-steroidal anti-inflammatory drug; (b) a compound having the structural formula I

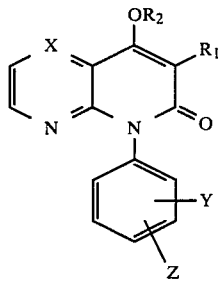

wherein

X is CH or N;

Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl-$S(O)_m$— having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;

Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;

$R_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, 2-, 3-, or 4-pyridyl, 2-, 4-, 5-pyrimidyl, 2- or 3-furanyl, 2- or 3-thienyl, carboxylic acyl having from 2 to 6 carbon atoms or alkyl having from 1 to 10 carbon atoms which may be substituted with hydroxy, halogen, —COOH, alkoxy having from 1 to 6 carbon atoms, phenyl, 2-, 3- or 4-pyridyl, 2-, 4- or 5-pyrimidyl, 2- or 3- thienyl, 2- or 3-furanyl, carboxylic acyl having from 2 to 6 carbon atoms, cycloalkyl having from 3 to 7 carbon atoms or carboxylic acyloxy having from 1 to 6 carbon atoms;

$R_2$ is hydrogen, alkenyl having from 3 to 8 carbon atoms, alkynyl having from 3 to 8 carbon atoms, carboxylic acyl having from 1 to 6 carbon atoms, $R_aR_bN(CH_2)_n$— (wherein $R_a$ and $R_b$ are hydrogen, alkyl having from 1 to 6 carbon atoms or may be joined to complete a piperidine, morpholine, piperazine or pyrrolidine ring and n is an integer of from 2 to 6) hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine; (c) a pharmaceutical carrier.

The compounds of formula I were evaluated for their anti-ulcer activity by standard biological procedures which measure their cytoprotective effect (also referred to as mucoprotective effects) in rats.

The standard cytoprotective tests were conducted in rats employing ethanol, aspirin or indomethacin to induce gastrointestinal damage as described in Robert et al., Gastroenterology, 77, 433–443 (1979), Lee et al., Arch. Int. Pharmacodyne, 191, 370–377 (1971), Dodge et al., Digestive Diseases, 19, 457 (1974) and Derelanko et al., Digestive Diseases, 25, 823–829 (1980). The compounds of Formula I were found to be effective for the oral amd parenteral treatment of the ulcerative disease states mentioned herein at doses of about 0.1 to 30 mg/kg of body weight per day.

In particular, the compounds of formula I are orally and parenterally effective in the relief of the symptoms of gastric ulcer diseases and promote the healing of gastric ulcers at a dosage range of 0.1 to 30 mg/kg of body weight per day, preferably 0.1 to 10 mg/kg.

The compounds of formula I are particularly effective for the treatment of intestinal ulceration or irritation. The protection afforded against intestinal ulceration is surprising in view of the fact that anti-ulcer H2 antagonists such as cimetidine (Tagamet ®) and ranitidine (Zantac ®) do not afford protection against intestinal ulceration. The compounds of formula I promote the relief of the symptoms of duodenal and intestinal ulcer diseases and promote the healing of duodenal and intestinal ulcers at an oral or parenteral dosage range of 10 to 30 mg/kg of body weight per day.

The usual dosage range for the compounds of formula I in a 70 kg person is an oral dose of about 20 to 2000 mg/day, preferably 20 to 700 mg/day, in 3 to 4 divided doses. Of course, the dose will be regulated according to the ulcer being treated (i.e., intestinal ulcers 10 to 30 mg/kg of body weight), the judgment of the attending clinician depending on factors such as the degree of severity of the disease state and age and general condition of the patient being treated.

To treat ulcer diseases, such as gastric, duodenal, and intestinal ulcers, the active compounds of formula I can be administered in unit dosage forms such as tablets, capsules, pills, powders, granules, sterile parenteral solutions or suspensions, suppositories and the like. Such dosage forms are prepared according to standard techniques well known in the art.

The non-steroidal anti-inflammatory agent may be administered either separately from or in combination with a compound of formula I. Any convenient, therapeutically useful route of administration may be utilized. Further, the components may be administered by different routes and at different times for purposes of efficacy and/or convenience.

The following examples illustrate the preparation of the compounds used in the methods of this invention as well as pharmaceutical compositions containing the compounds. All temperatures are in degrees Celsius.

EXAMPLE 1

3-(n-Butyl)-4-hydroxy-1-(3-methylthiophenyl)-1,8-naphthyridin-2(1H)one

To a stirred solution of 11 g. of methyl 2-(3-methylthiophenylamino)-3-pyridine carboxylate in 110 ml. of ethyl caproate there is added, portionwise, 8.96 g. of potassium tertiary butoxide in an atmosphere of nitrogen. The reaction mixture is heated to an internal temperature of 140°–142° for two hours, cooled and the potassium salt is collected by filtration. The crude potassium salt is dissolved in 150 ml of water, acidified with 10% hydrochloric acid and the product filtered and dried; weight 12.1 g., m.p. 245°–246° C. Recrystallization from pyridine-ether gives a colorless solid, m.p. 245°–246° C.

Prepare the 3-(n-butyl)-4-hydroxy-1-phenyl-1,8-naphthyridin-2(1H)one by the process of Example 1 by replacing the methyl 2-(3-methylthiophenylamino)-3-pyridine carboxylate with an equivalent amount of methyl 2-phenylamino-3-pyridine carboxylate.

EXAMPLE 1A

4-Hydroxy-1-phenyl-1,8-naphthyridin-2(1H)-one

To a stirred solution of 1 kg. of methyl 2-phenylamino-3-pyridine carboxylate in 3.97 liters of n-butyl acetate there is added portionwise, 1.1 kg. of potassium tertiary butoxide. After the addition of the potassium tertiary butoxide, there is added an additional 1.32 liters of n-butyl acetate. The reaction mixture is heated to reflux for 20 hours during which the internal temperature of the reaction mixture rose from 90° C. to 122° C. During this period, 1.8 liters of liquid is removed from the reaction mixture via a Dean-Stark trap. Xylene (3.0 liters) is added to the reaction mixture and the remainder of the n-butyl acetate is removed via the Dean-Stark trap. The reaction mixture is cooled and the potassium salt is collected by filtration, washed with toluene and air dried. The crude potassium salt is dissolved in 12 liters of water, the aqueous solution is extracted with toluene, acidified to pH 2 and the product filtered and dried; weight 937 g., m.p. 311°–313° C.

EXAMPLE 2

3-(n-Butyl)-4-hydroxy-1-phenyl-1,8-naphthyridine-2(1H)-one sodium salt

Add 57.9 ml of 1N sodium hydroxide aqueous solution to a stirred suspension of 17.05 g of 3-(n-butyl)-4-hydroxy-1-phenyl-1,8-naphthyridine-2(1H)-one and 140 ml of water. Stir for one hour at room temperature, cool in an ice bath and filter. Lyophilize the clear filtrate overnight to give the title compound as a monohydrate. It is a cream colored powder, m.p. 240°–260° C. (decomposition).

Prepare the corresponding potassium salt as a monohydrate by the process of Example 2 by replacing the sodium hydroxide aqueous solution with an equivalent amount of potassium hydroxide aqueous solution. The lyophilized potassium salt has a melting point of 215°–225° C.

EXAMPLE 3

3-(n-Butyl)-4-hydroxy-1-phenyl-1,8-naphthyridine-2(1H)-one ethanolamine salt

Add 0.65 g of ethanolamine to 2.9 gm of 3-(n-butyl)-4-hydroxy-1-phenyl-1,8-naphthyridine-2(1H)-one in 100 ml of methanol. Remove the solvent in vacuo and add ethyl acetate to precipitate the title compound as a colorless salt, m.p. 228°–234°.

Prepare the following amine salts by the process of Example 3 by replacing the ethanolamine with the corresponding amine.

3-(n-Butyl)-4-hydroxy-1-phenyl-1,8-naphthyridine-2(1H)-one N-methylglucamine salt, melting point 181°–206°.

3-(n-Butyl)-4-hydroxy-1-phenyl-1,8-naphthyridine-2(1H)-one diethanolamine salt, melting point 160°–190°.

3-(n-Butyl)-4-hydroxy-1-phenyl-1,8-naphthyridine-2(1H)-one ethylenediamine salt, melting point 158°–171°.

EXAMPLE 4

3-(n-Butyl)-4-hydroxy-1-phenyl-1,8-naphthyridine-2(1H)-one calcium salt

Treat a aqueous solution of 1 g (3 m moles) of the compound of Example 2 herein with 1.5 ml of 1N calcium chloride solution (1.5 m moles). Filter the resulting cloudy solution and allow to stand until a precipitate forms. Filter and wash with acetone. Recover the title compound from water or acetone-water as a pentahydrate which is a colorless powder, m.p. >350°.

EXAMPLE 5

4-Acetoxy-1-phenyl-3-(2-propenyl)-1,8-naphthyridine-2(1H)-one (A) 4-(2-propenyloxy)-1-phenyl-1,8-naphthyridin-2(1H)-one:

To a mixture of 62 g. of 4-hydroxy-1-phenyl-1,8-naphthyridin-2(1H)-one, 39.6 g. of anhydrous potassium carbonate and 1,800 ml of acetone there is added dropwise, with stirring, 37.5 g. of allyl bromide. The reaction mixture is refluxed for 22 hours, concentrated in vacuo, and the residue extracted with 600 ml. of chloroform. The organic extract is washed with water, 1N sodium hydroxide solution and again with water, dried over anhydrous magnesium sulfate, filtered and concentrated. The crude solid is triturated with 3×400 ml of boiling isopropyl ether, filtered, yielding the insoluble product, wt. 38.5 g. m.p. 171°–174°. Recrystallization from methanol produces the product as a colorless solid, m.p. 176°–177° C.

(B) 4-Acetoxy-1-phenyl-3-(2-propenyl)-1,8-naphthyridin-2(1H)-one:

A mixture of 33.8 g. of 4-(2-propenyloxy)-1-phenyl-1,8-naphthyridin-2(1H)-one and 35 ml. of acetic anhydride is refluxed for four hours. On cooling, the reaction mixture solidified. Trituration with isopropyl ether and filtration yields the product, 36.1 g., as a colorless solid, m.p. 189°–195° C. Recrystallization from ethanol provides the product of this example melting at 195°–196° C.

EXAMPLE 6

4-Hydroxy-1-phenyl-3-(2-propenyl)-1,8-naphthyridin-2(1H)-one

A mixture of 6.0 g. of 4-acetoxy-1-phenyl-3-(2-propenyl)-1,8-naphthyridin-2(1H)-one, 200 ml. of ethanol and 40 ml. of 1N sodium hydroxide solution is stirred at room temperature for 22 hours. The ethanol is removed in vacuo and the remaining aqueous solution acidified with 1N hydrochloric acid. The product is filtered, washed with water and dried, weight 5.3 g., m.p. 248°–250° C. Recrystallization from chloroform yields the product of this example as a colorless solid, m.p. 250°–252° C.

EXAMPLE 7

7-(n-Butyl)-8-hydroxy-5-phenylpyrido[2,3-b]pyrazine-6(5H)-one (A) Methyl 2-bromo-3-pyrazine carboxylate:

To a stirred mixture of 12.7 g. of methyl 2-aminopyrazine 3-carboxylate and 47 ml. of 48% hydrobromic acid there is added, dropwise, 12.6 ml. of bromine keeping the temperature at 0°. A solution of 14.4 g. of sodium nitrite in 60 ml. of water is then added, dropwise, at 0° and the reaction mixture stirred for 15 minutes. The reaction mixture is basified to pH 8 with sodium bicarbonate and extracted with ethyl acetate and again with chloroform. The organic layers are dried over magnesium sulfate, filtered and concentrated to a yellow oil. Recrystallization from ether-hexane yields the product, m.p. 43°–45° C.

(B) Methyl 2-phenylamino-3-pyrazine carboxylate:

A mixture of 9.5 g. of methyl 2-bromo-3-pyrazine carboxylate, 8.2 g. of aniline, 0.5 g. of p-toluene sulfonic acid and 100 ml. of water is stirred and refluxed for two hours. The reaction mixture is poured on ice, extracted with ethyl acetate, the organic extracts are dried and concentrated to yield an oil. The crude residue is eluted on a silica gel column with ethylacetate-hexane (1:2) yielding the product of this example as a yellow solid, m.p. 72°–75° C.

(C) 7-(n-Butyl)-8-hydroxy-5-phenyl-pyrido[2,3-b]pyrazine-6(5H)one:

A mixture of 3.5 g. of methyl 2-phenylamino-3-pyrazine carboxylate, 30 ml. of ethyl caproate and 4 g. of potassium tertiary butoxide is stirred and heated under nitrogen at 150°–160° for one and a half hours. The reaction mixture is poured on ice, extracted with ethyl acetate and the ethyl acetate extracts washed with water. The combined aqueous layers are acidified to pH 5.5 with dilute hydrochloric acid and the solid filtered. Recrystallization from ethyl acetate-hexane yields the product of this example as a colorless solid; m.p. 183°–185° C.

EXAMPLE 8

3-(2-Hydroxyethyl)-4-hydroxy-1-phenyl-1,8-naphthyridin-2(1H)one

To a solution of 6.8 g. of methyl 2-phenylamino-3-pyridine carboxylate in 60 ml. of gammabutyrolactone there is added, under nitrogen, 13.4 g. of potassium tertiary butoxide. The reaction mixture is heated and stirred for one hour at 95° C., poured on ice and stirred overnite. The mixture is extracted with ether, the aqueous layer acidified with acetic acid to pH 4.5 and the product is collected by filtration. Recrystallization from chloroform, acetone, isopropanol yields the product of this example as a colorless solid; m.p. 235°–236° C.

EXAMPLE 9

4-Hydroxy-1-phenyl-3-(2-pyridyl)-1,8-naphthyridin-2(1H)one

To a stirred solution of 5.8 gm of methyl2-phenylamino-3-pyridine carboxylate and 25 gm of ethyl 2-pyridylacetate there is added, portionwise, 5.7 gm of potassium tertiary butoxide under a nitrogen atmosphere. The system is heated to an internal temperature of 105° C. for 10 minutes. The reaction is cooled to room temperature, diluted with 100 ml of diethyl ether and the brown precipitate is collected by filtration. The precipitate is washed with 200 ml water and the filtrate is acidified to pH 3–4 with a 15% HCl solution whereupon the product separates. The precipitate is filtered and dried to give 6.3 gm of crude 4-hydroxy-1-phenyl-3-(2'-pyridyl)-1,8-naphthyridin-2(1H)one; m.p. 308°–310° C. Recrystallization from pyridine yields the title product; m.p. 332°–333° C.

EXAMPLE 10

3-(n-Butyl)-4-(2-hydroxyethoxy)-1-phenyl-1,8-naphthyridin-2(1H)one

Reflux a stirred solution of 16.2 gm of 3-(n-butyl)-4-hydroxy-1-phenyl-1,8-naphthyridin-2(1H)-one and 11.4 gm of anhydrous potassium carbonate powder in 600 ml of dry acetone for 30 minutes. 95% 2-bromoethanol (10.3 gm) is added dropwise to the solution. The reaction is refluxed for 26 hours, cooled and the solvent removed by stripping. The resulting solid is dissolved in 500 ml chloroform and the chloroform solution is washed with 300 ml water, twice with 100 ml of 0.5N sodium hydroxide solution and finally with 100 ml of water. The chloroform solution is dried over magnesium sulfate, filtered and the solvent is removed to give the crude product. The crude product is triturated with warm isopropyl ether to give 10.9 gm of the 3-(n-butyl)-4-(2-hydroxyethoxy)-1-phenyl-1,8-naphthyridin-2(1H)one; which after recrystallization from acetone melts at 138°–140° C.

EXAMPLE 11

3-(n-Butyl)-4-[2-(2-hydroxyethoxy)ethoxy]-1-phenyl-1,8-naphthyridin-2(1H)one

To a mixture of 6.8 g of 3-(n-butyl)-4-(2-hydroxyethoxy)-1-phenyl-1,8-naphthyridin-2(1H)one and 150 ml of anhydrous dioxane there is added 0.8 g of sodium hydride (60% oil dispersion) with stirring. The reaction mixture is stirred and warmed on a steam bath for 30 minutes, followed by the dropwise addition of 2.6 g of 95% 2-bromoethanol. The reaction mixture is stirred and refluxed for 24 hours, the solvent is removed in vacuo and the residual solid is dissolved in chloroform. The chloroform solution is successively washed with water, 0.5N sodium hydroxide and water. The organic layer is dried over magnesium sulfate, filtered and concentrated to dryness to yield the product of this example.

The following formulations exemplify some of the dosage forms of the compositions of this invention. In each, the term "active compound" designates a compound of formula I.

PHARMACEUTICAL DOSAGE FORM EXAMPLES

EXAMPLE A

| | Tablets | | |
|---|---|---|---|
| No. | Ingredient | mg/tablets | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixture for 10-15 minutes. Granulate the mixture with Item No. 3. Mill the damp granules through a coarse screen (e.g., ¼") if needed. Dry the damp granules. Screen the dried granules if needed and mix with Item No. 4 and mix for 10-15 minutes. Add Item No. 5 and mix for 1-3 minutes. Compress the mixture to appropriate size and weight on a suitable tablet machine.

EXAMPLE B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

EXAMPLE C

| Parenteral | | |
|---|---|---|
| Ingredient | mg/vial | mg/vial |
| Active Compound Sterile Powder | 100 | 500 |

Add sterile water for injection or bacteriostatic water for injection for reconstitution.

EXAMPLE D

| | Injectable | |
|---|---|---|
| Ingredient | mg/vial | mg/vial |
| Active Compound | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°-70° C.
2. Cool to 25°-35° C. Charge and dissolve the sodium bisulfite, disodium edetate and sodium sulfate.
3. Charge and dissolve drug.
4. Bring the solution to final volume by added water for injection.
5. Filter the solution through 0.22 membrane and fill into appropriate containers.
6. Terminally sterilize the units by autoclaving.

The following formulations exemplify some of the dosage forms of the compositions of the invention which employ a combination of a compound of formula I plus a non-steroidal anti-inflammatory agent. In each, the term "active compound" designates a compound of formula I.

EXAMPLE E

| | Capsules | | |
|---|---|---|---|
| No. | Ingredient | mg/capsule | mg/capsule |
| 1. | Active compound | 100 | 500 |
| 2. | Indomethacin | 25 | 50 |
| 3. | Lactose USP | 106 | 73 |
| 4. | Corn Starch, Food Grade | 40 | 70 |
| 5. | Magnesium Stearate NF | 4 | 7 |
| | Total | 275 | 700 |

Method of Manufacture

Mix Item Nos. 1, 2, 3 and 4 in a suitable mixer for 10-15 minutes. Add Item No. 5 and mix for 1-3 minutes. Fill the mixture into suitable two-piece hard gelatin capsules using suitable encapsulating machine.

| No. | Ingredient | mg/capsule | mg/capsule |
|---|---|---|---|
| 1. | Active compound | 100 | 500 |
| 2. | Aspirin | 325 | 325 |
| 3. | Lactose USP | 106 | 25 |
| 4. | Corn Starch, Food Grade | 40 | 25 |
| 5. | Magnesium Stearate NF | 4 | 5 |
| | Total | 575 | 880 |

Method of Manufacture

Mix Item Nos. 1, 2, 3 and 4 in a suitable mixer for 10-15 minutes. Add Item No. 5 and mix for 1-3 minutes. Fill the mixture into suitable two-piece hard gelatin capsules using suitable encapsulating machine.

EXAMPLE F

| No. | Ingredient | Tablets mg/capsule | mg/capsule |
|---|---|---|---|
| 1. | Active compound | 100 | 500 |
| 2. | Sulindac | 150 | 200 |
| 3. | Lactose USP | 122 | 43 |
| 4. | Corn Starch, Food Grade, as a 10% paste in Purified Water | 30 | 40 |
| 5. | Corn Starch, Food Grade | 45 | 40 |
| 6. | Magnesium Stearate NF | 3 | 7 |
|  | Total | 450 | 830 |

Mixture of Manufacture

Mix Item Nos. 1, 2 and 3 in a suitable mixer for 10–15 minutes. Granulate the mixture with Item No. 4. Pass the wet granulation through a coarse screen (e.g., ¼″) if needed, and dry the wet granules. Mill the dried granules. Combine Item No. 5 and the dried granules and mix for 10–15 minutes. Add Item No. 6 and mix for 1–3 minutes. Compress the mixture to appropriate size and weight on a suitable tablet machine.

I claim:

1. A composition for inhibiting the formation of a non-steroidal anti-inflammatory drug-induced ulceration which comprises;
(a) a non-steroidal anti-inflammatory drug;
(b) a compound having the structural formula I:

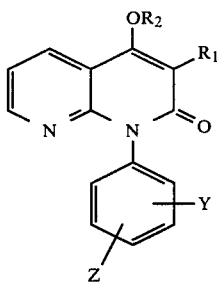

I wherein

Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl-S(O)$_m$— having from 1 to 6 carbon atoms wherein m is 0, 1, or 2, trifluoromethyl, trifluromethylthio, or COOA wherein A is hydrogen, alkyl having from 1 to 6 carbon atoms or a cation derived from a pharmaceutically acceptable metal or an amine;

Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;

R$_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, carboxylic acyl having from 2 to 6 carbon atoms or alkyl having from 1 to 10 carbon atoms which may be substituted with hydroxy, COOH, halogen, alkoxy having from 1 to 6 carbon atoms, phenyl, carboxylic acyl having from 2 to 6 carbon atoms, cycloalky having from 3 to 7 carbon atoms or carboxylic acyloxy having from 1 to 6 carbon atoms;

R$_2$ is hydrogen, alkenyl having from 3 to 8 carbon atoms, alkynyl having from 3 to 8 carbon atoms, carboxylic acyl having from 1 to 6 carbon atoms, alkyl having from 1 to 6 carbon atoms, R$_a$R$_b$N(CH$_2$)$_n$— (wherein R$_a$ and R$_b$ are hydrogen, alkyl having from 1 to 6 carbon atoms, and n is an integer of from 2 to 6) hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine;

(c) and a pharmaceutical carrier.

2. A composition for inhibiting the formation of a non-steroidal anti-inflammatory drug-induced ulceration which comprises (a) a non-steroidal anti-inflammatory drug; (b) a compound selected from the group

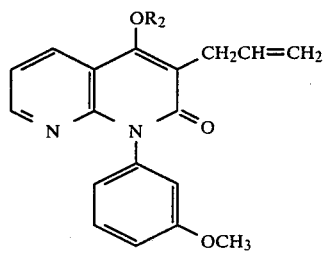

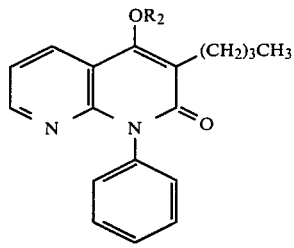

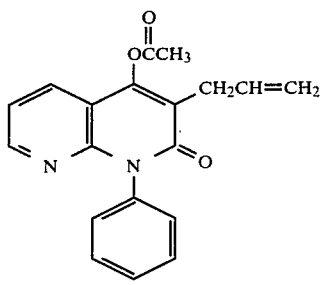

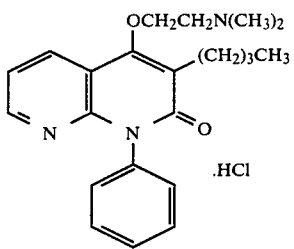

wherein R$^2$ is hydrogen or sodium; and (c) a pharmaceutical carrier.

3. A composition according to claim 2 wherein the non-steroidal anti-inflammatory drug is aspirin.

4. A composition according to claim 2 wherein the non-steroidal anti-inflammatory drug is phenylbutazone.

5. A composition according to claim 2 wherein the non-steroidal anti-inflammatory drug is isoxicam.

6. A composition according to claim 2 wherein the non-steroidal anti-inflammatory drug is piroxicam.

7. A composition according to claim 2 wherein the non-steroidal anti-inflammatory drug is indomethacin.

8. A composition according to claim 2 wherein the non-steroidal anti-inflammatory drug is naproxen.

9. A composition according to claim 2 wherein the non-steroidal anti-inflammatory drug is ibuprofen.

10. A composition for inhibiting the formation of a non-steroidal anti-inflammatory drug-induced ulceration which comprises:
  (a) a non-steroidal anti-inflammatory drug;
  (b) a compound selected from the group
    1-phenyl-4-propionyloxy-3(4-propionyloxybutyl)-1,8-naphthyridin-2(1H)-one;
    3-(n-butyl)-4-hydroxy-1-(3-methylthiophenyl-1,8-naphthyridine-2(1H)-one;
    3-(n-butyl)-4(2-hydroxyethoxy)-1-phenyl-1,8-naphthyridin-2(1H)-one;
    4-hydroxy-3(3-hydroxypropyl)-1-phenyl-1,8-naphthyridin-2(1H)-one; and
  (c) a pharmaceutical carrier.

* * * * *